US009192331B2

(12) United States Patent
Cha et al.

(10) Patent No.: US 9,192,331 B2
(45) Date of Patent: Nov. 24, 2015

(54) RELEASING STRUCTURE FOR LANCING DEVICE

(75) Inventors: Geun Sig Cha, Seoul (KR); Hakhyun Nam, Seoul (KR); Eun-Jong Cha, Cheongju-si (KR); Kyung-Ah Kim, Cheongju-si (KR)

(73) Assignee: I-SENS, INC., Seoul (KR)

( * ) Notice: Subject to any disclaimer, the term of this patent is extended or adjusted under 35 U.S.C. 154(b) by 217 days.

(21) Appl. No.: 13/993,059

(22) PCT Filed: Sep. 20, 2011

(86) PCT No.: PCT/KR2011/006934
§ 371 (c)(1),
(2), (4) Date: Jun. 17, 2013

(87) PCT Pub. No.: WO2012/081807
PCT Pub. Date: Jun. 21, 2012

(65) Prior Publication Data
US 2013/0274781 A1 Oct. 17, 2013

(30) Foreign Application Priority Data

Dec. 14, 2010 (KR) ........................ 10-2010-0127791

(51) Int. Cl.
*A61B 5/151* (2006.01)
*A61B 5/15* (2006.01)

(52) U.S. Cl.
CPC ........... *A61B 5/15126* (2013.01); *A61B 5/1411* (2013.01); *A61B 5/1519* (2013.01); *A61B 5/15113* (2013.01); *A61B 5/15117* (2013.01); *A61B 5/15128* (2013.01);

(Continued)

(58) Field of Classification Search
CPC ............... A61B 5/1411; A61B 5/1433; A61B 5/15029; A61B 5/15117; A61B 5/15126; A61B 5/15128; A61B 5/1513; A61B 5/15132; A61B 5/1519; A61B 5/15192; A61B 5/15194; A61B 5/15196; A61B 5/15198; A61B 5/150183; A61B 5/15019; A61B 5/140198
USPC ............. 606/181, 182; 604/117, 110, 164.01, 604/164.12
See application file for complete search history.

(56) References Cited

U.S. PATENT DOCUMENTS 4,517,978 A * 5/1985 Levin et al. .................... 606/182
5,318,584 A * 6/1994 Lange et al. .................. 606/182

(Continued)

FOREIGN PATENT DOCUMENTS

CN 1658791 A 8/2005
CN 1764413 A 4/2006

(Continued)

*Primary Examiner* — Todd Manahan
*Assistant Examiner* — Casey B Lewis
(74) *Attorney, Agent, or Firm* — McDermott Will & Emery LLP

(57) ABSTRACT

A releasing structure for a lancing device according to an exemplary embodiment of the present invention may include: a lancet body with a lancet at the front; a lancet holder mounted with the lancet body with the lancet at the front; a stem disposed behind the lancet holder and moving the lancet holder forward/backward; a rotary housing pushing/pulling the stem while turning forward at a predetermined angle about a rotational axis defined in the movement direction of the lancet; a torsion spring storing torque for turning the rotary housing forward at a predetermined angle; and a loading handle transmitting torque to the torsion spring while turning forward at a predetermined angle.

9 Claims, 11 Drawing Sheets

(52) U.S. Cl.
CPC .......... *A61B 5/15194* (2013.01); *A61B 5/1513* (2013.01); *A61B 5/150022* (2013.01); *A61B 5/150068* (2013.01); *A61B 5/150114* (2013.01); *A61B 5/150183* (2013.01); *A61B 5/150412* (2013.01); *A61B 5/150519* (2013.01); *A61B 5/150664* (2013.01)

(56) References Cited

U.S. PATENT DOCUMENTS

| | | | |
|---|---|---|---|
| 5,423,847 A * | 6/1995 | Strong et al. | 606/182 |
| 6,156,050 A * | 12/2000 | Davis et al. | 606/181 |
| 7,175,641 B1 * | 2/2007 | Schraga | 606/182 |
| 7,510,564 B2 * | 3/2009 | Mace | 606/181 |
| 2002/0169470 A1 * | 11/2002 | Kuhr et al. | 606/182 |
| 2004/0127929 A1 * | 7/2004 | Roe | 606/181 |
| 2005/0234487 A1 | 10/2005 | Shi | |
| 2007/0173874 A1 | 7/2007 | Uschold et al. | |
| 2010/0145377 A1 * | 6/2010 | Lai et al. | 606/182 |

FOREIGN PATENT DOCUMENTS

| | | |
|---|---|---|
| CN | 101664312 A | 3/2010 |
| DE | 10223558 A1 | 12/2003 |
| EP | 0565970 A1 | 10/1993 |
| JP | 2001-087251 A | 4/2001 |
| JP | 2008-511354 A | 4/2008 |
| KR | 1020050032194 A | 4/2005 |
| KR | 1020070077106 A | 7/2007 |
| KR | 1020100114710 A | 10/2010 |
| WO | 2006/027101 A1 | 3/2006 |

* cited by examiner

View 8A

RELEASING STRUCTURE FOR LANCING DEVICE

FIELD OF THE INVENTION

The present invention relates to a releasing structure for a lancing device. More particularly, the present invention relates to a releasing structure for a lancing device that helps taking blood from a patient by moving forward/backward a lancet for taking blood at a high speed.

DESCRIPTION OF THE RELATED ART

In general, chronic diabetics have to measure the blood glucose level by performing a blood sugar test by themselves everyday at home and to perform disease control in order to keep a predetermined blood glucose level.

They have to collect blood for the blood glucose test, and this case, generally, they stick a disposable lancet into the skin of a portion, usually a finger, of their bodies, take and put a small amount of capillary blood onto a strip, and then measure the blood glucose level using a blood glucose meter with the strip mounted.

A lancing device is generally used as the device for taking blood.

The lancing device is composed of a lancet holder mounted with a disposable lancet, a cover that covers a lancet and has a hole through which only the tip of a needle protrudes to penetrate a skin, and a spring and a releasing member that provide a penetration force.

The disposable lancet has a needle at one end of a lancet body and a protection cap is combined with the needle.

According to the lancing devices having this configuration in the related art, a user removes the cover from a lancing device, mounts a disposable lancet onto the lancet holder, attaches the cover with the spring compressed, brings the lancet in close contact with a portion with many capillaries such as fingers, and then releases the disposable lancet by pulling a releasing switch, such that the lancet penetrates the skin.

As an example, a technology that releases a lancet forward by mounting a lancet, pulling a sleeve back, and then pressing a trigger so that a needle instantaneously penetrates a skin and then moves back has been disclosed in U.S. Pat. No. 4,517,978.

In general, a lancet is mounted on a lancing device and then released, in which the lancet is supposed to move forward through a skin and then return, but the lancet is stuck in the skin of a patient in some cases, such that it is difficult to take blood and the pain of the patient increases.

DISCLOSURE

Technical Problem

The present invention has been made in an effort to provide a releasing structure for a lancing device having advantages of making it easy to take blood and reducing the pain of a patient by releasing a lancet mounted on a lancing device and stably returning the lancet.

Technical Solution

An exemplary embodiment of the present invention provides releasing structure for a lancing device, which may include: a lancet body with a lancet at the front; a lancet holder mounted with the lancet body with the lancet at the front; a stem disposed behind the lancet holder and moving the lancet holder forward/backward; a rotary housing pushing/pulling the stem while turning forward at a predetermined angle about a rotational axis defined in the movement direction of the lancet; a torsion spring storing torque for turning the rotary housing forward at a predetermined angle; and a loading handle transmitting torque to the torsion spring while turning forward at a predetermined angle.

The lancet body, the lancet holder, the stem, the rotary housing, the torsion spring, and the loading handle may be sequentially arranged on a rotation center axis defined in the movement direction of the lancet.

The structure may further include a case in which at least a portion of the lancet body, the lancet holder, the stem, the rotary housing, the torsion spring, or the loading handle is inserted, in which an anti-reverse protrusion that prevents the loading handle from reversing may be formed on the outer side of the loading handle and a locking protrusion corresponding to the anti-reverse protrusion may be formed on the inner side of the case, and the anti-reverse protrusion may be locked to the locking protrusion, after the loading handle transmits torque to the torsion spring by turning at a predetermined angle, such that the loading handle may be prevented from reversing.

A locking protrusion may be formed on the outer side of the rotary housing, at a predetermined distance from the rotation center axis, and the structure may include: a locker mounted on a side of the case and having an anti-releasing protrusion for preventing turning of the rotary housing by engaging with the locking protrusion; a releasing spring elastically supporting the locker to keep the anti-releasing protrusion engaging with the locking protrusion; and a releasing switch mounted on the case and pushing the locker against the elastic force of the releasing spring so that the anti-releasing protrusion is unlocked from the locking protrusion and the rotary housing is turned by the torque stored in the torsion spring.

One end of the stem may be connected to the lancet holder by a connection pin and the other end may be inserted in the rotary housing, a disc formed radially from the rotation center axis of the stem in the rotary housing may be formed on the portion of the stem which is inserted in the rotary housing, a forward-inclined rib inclined within a predetermined range of angle in the rotation direction may be formed on the rear side of the disc and a backward-inclined rib corresponding to the forward-inclined ribs may be formed on the front side of the disc, a forward rib may protrude at a side on the inner side of the rotary housing with the stem inserted, corresponding to the forward-inclined rib, and push the stem forward by moving along the inclined surface of the forward-inclined rib while turning with the rotary housing, and a backward rib may protrude at the other side on the inner side of the rotary housing, corresponding to the backward-inclined rib, and push the stem backward by moving along the inclined surface of the backward-inclined rib while turning with the rotary housing.

Two forward-inclined ribs may be formed with a gap of 180 degrees in the rotation direction on the rear side of the disc, and two backward-inclined ribs may be formed with a gap of 180 degrees in the rotation direction on the front side of the disc, corresponding to the forward-inclined ribs.

The forward rib may come in close contact with the inclined surfaces of the forward-inclined ribs while turning with the rotary housing so that the stem moves forward, the backward rib may come in close contact with the inclined surfaces of the backward-inclined ribs while turning with the rotary housing so that the stem moves backward, and the forward-inclined ribs and the backward-inclined ribs may have a rotational difference of 90 degrees in the turning direction of the rotary housing.

The forward rib may be in contact with the rear side of the disc, with the rotary housing turned 0 degrees, before releasing, as the rotary housing turns 90 degrees, the forward rib may push the stem forward by moving along the inclined surface of the forward-inclined rib and the backward rib may be adjacent to the front side of the disc, and as the rotary housing turns 180 degrees, the backward rib may move the stem backward by moving along the inclined surface of the backward-inclined rib.

The inclined surface of the forward-inclined rib may be formed within the range of 90 degrees in the turning direction of the rotary housing.

An indication hole may be formed at the case and the turning position of the loading handle or the rotary housing may be sensed through the indication hole.

As described above, according to the releasing structure for a lancing device of the present invention, it is possible to easily store releasing energy in a torsion spring, using a loading handle.

Further, it is possible to easily prevent a lancet from being stuck in the skin of a user (patient) by moving forward/backward a stem connected with a lancet, using a forward rib and a backward rib on the inner side of a rotary housing.

Further, while the rotary housing turns, a forward rib on the inner side of the rotary housing moves the stem forward, using forward-inclined ribs on the rear side of the disc of the stem and the backward rib on the inner side of the rotary housing at a predetermined distance from the forward rib moves the stem backward, using backward-inclined ribs on the front side of the disc of the stem.

BEST MODE

An exemplary embodiment of the present invention will hereinafter be described in detail with reference to the accompanying drawings.

Figure 1:
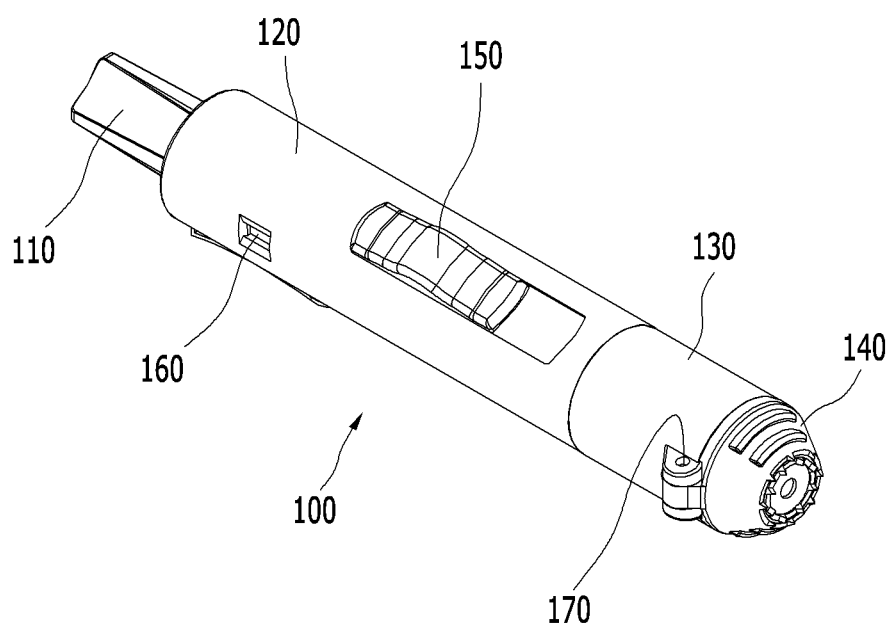
FIG. 1 is a schematic perspective view of a lancing device according to an exemplary embodiment of the present invention.
Figure 2:
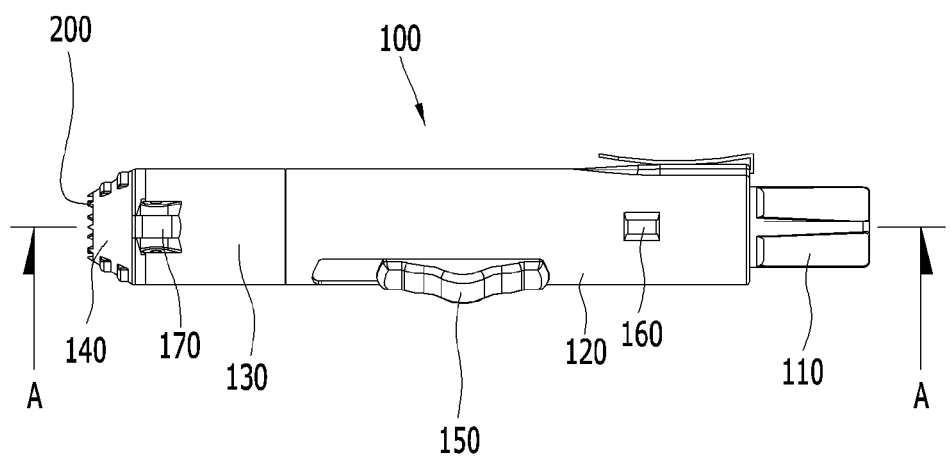
FIG. 2 is a top plan view of the lancing device according to an exemplary embodiment of the present invention.

FIG. 1 is a schematic perspective view of a lancing device according to an exemplary embodiment of the present invention and FIG. 2 is a top plan view of the lancing device according to an exemplary embodiment of the present invention.

Referring to FIGS. 1 and 2, a lancing device 100 includes a main case 120, a front case 130, a cap 140, and a loading handle 110. The main case 120 and the front case 130 form the main external body and the cap 140 is disposed ahead of the front case 130 and combined with the front case 130 by a hinge 170.

The loading handle 110 is inserted into the main case 120 from behind, and when a user (patient) turns the loading handle 110 forward at a predetermined angle (for example, 180 degrees) and presses the releasing switch 394 (in FIG. 3), the lancet 320 (in FIG. 3) moves forward/backward.

In an exemplary embodiment of the present invention, since the loading handle 110 is not longitudinally pushed, but turned, it is possible to easily check whether the lancet is loaded, from an indication hole 160 formed at the main case 120 in accordance with the turning position of the loading handle 110.

When a user opens the cap 140 and moves forward a discharge switch 150 on the main case 120, a lancet body 310 (in FIG. 3) is drawn out of a lancet holder 340 (in FIG. 3), such that it can be easily replaced by a new lancet unit.

Further, pressing protrusions 220 that distribute a pain in close contact with the skin of a user (patient), when the lancet 320 instantaneously penetrates the skin is formed around the releasing hole 300 at the front end of the cap.

Figure 3:
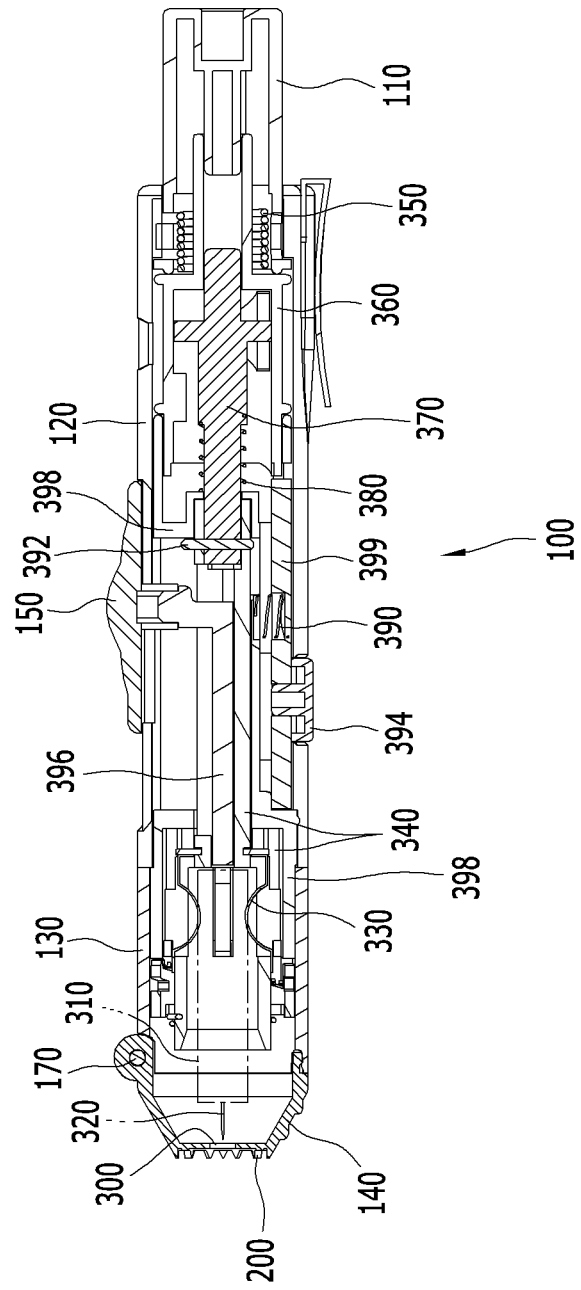
FIG. 3 is a cross-sectional view of the lancing device taken along line A-A in FIG. 2.
Figure 4:
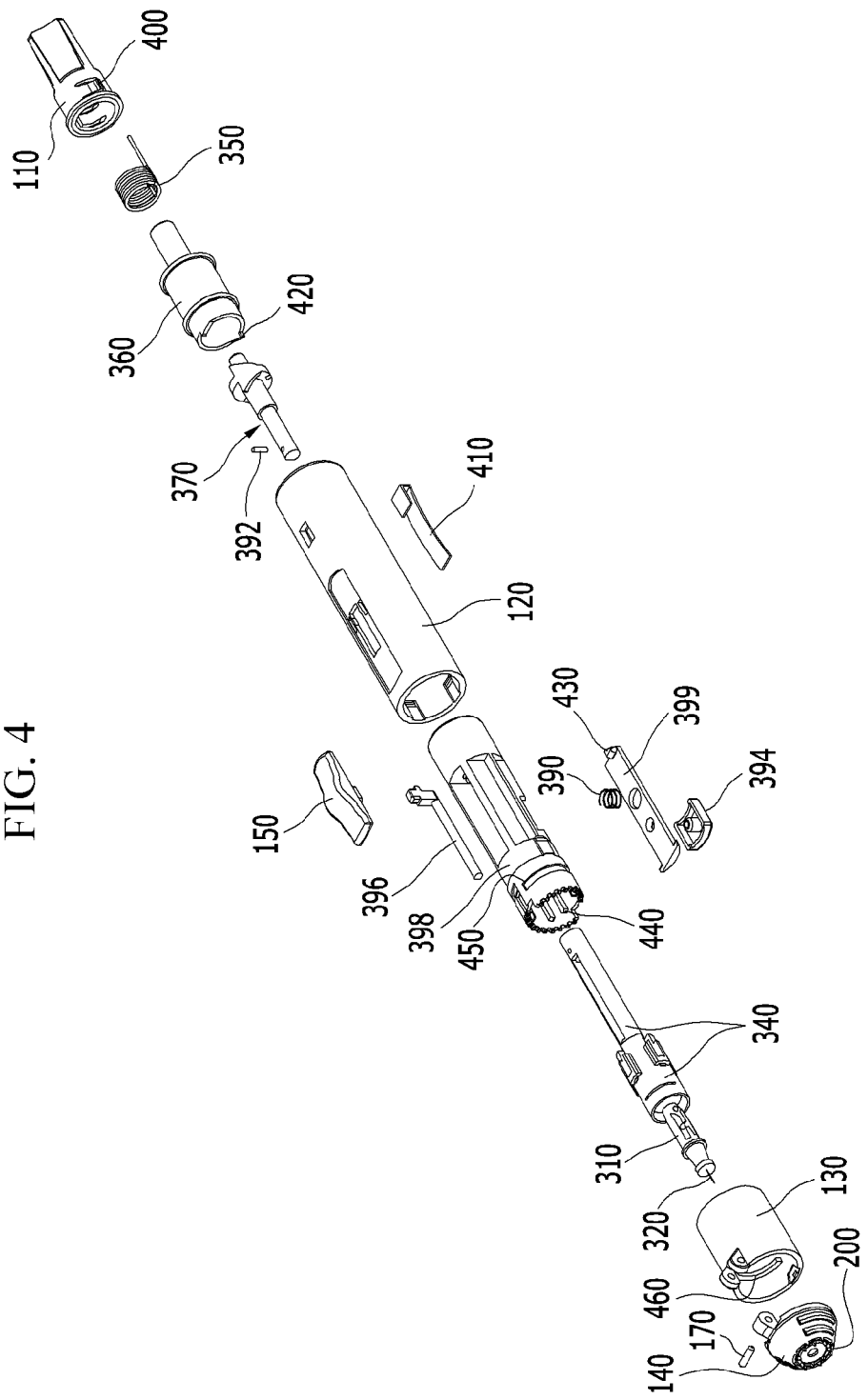
FIG. 4 is an exploded perspective view of the lancing device according to an exemplary embodiment of the present invention.

FIG. 3 is a cross-sectional view of the lancing device taken along line A-A in FIG. 2 and FIG. 4 is an exploded perspective view of the lancing device according to an exemplary embodiment of the present invention.

Referring to FIGS. 3 and 4, the lancing device 100 includes the loading handle 110, a torsion spring 350, a rotary housing 360, a stem 370, the main case 120, a clip 410, a holder housing 398, a discharge bar 396, the discharge switch 150, a releasing spring 390, a locker 399, the releasing switch 394, the lancet holder 340, the front case 130, the hinge 170, and the cap 140.

An anti-reverse protrusion 400 is formed on the outer side of the loading handle 110 and a locking protrusion (not shown) or a locking groove (not shown) corresponding to the anti-reverse protrusion 400 is formed on the inner side of the main case 120. Therefore, the loading handle 110 is prevented from turning backward after turning forward as much as the predetermined amount.

The torsion spring 350 is disposed between the rotary housing 360 and the loading handle 110, and when the rotary housing 360 is turned forward at 180 degrees, torque is stored in the torsion spring 350. One end of the torsion spring 350 is fixed to the loading handle 110 and the other end is fixed to the rotary housing 360.

That is, when a user turns the loading handle 110 at 180 degrees with the rotary housing 360 locked, corresponding torque is stored in the torsion spring 350. The torsion spring 350 is connected to one end of the rotary housing 360 and locking protrusions 420 are formed at an interval of 180 degrees at the other end.

Anti-releasing protrusions 430 corresponding to the locking protrusions 420 are formed at one end of the locker 399 and elastically supported by the releasing spring 390 while keeping locked to the locking protrusions 420.

When a user presses the releasing switch 394 combined with the locker 399, the locker 399 moves into the main case 120 against the elastic force of the releasing spring 390 and the anti-locking protrusions 430 on the locker 399 are unlocked from the locking protrusions 420, such that the rotary housing 360 is turned 180 degrees by the torque stored in the torsion spring 350.

While the rotary housing 360 turns 180 degrees, the stem 370 moves forward at the rotational position of 90 degrees and moves backward at the rotational position of 180 degrees.

Referring to FIGS. 3 and 4, the rear portion of the stem 370 is inserted in the rotary housing 360 and the front portion of the stem 370 is connected with the lancet holder 340 by a connection pin 392.

Further, the lancet holder 340 and the stem 370 move together longitudinally, that is, forward/backward and they are prevented from turning by an axial guide 440 formed on the inner side of the holder housing 398. Therefore, as the rotary housing 360 turns, the stem 370 and the lancet holder 340 only longitudinally reciprocate forward/backward.

The lancet 320 is disposed at the front end of the lancet body 310 inserted in the lancet holder 340 and an elastic support member 330 elastically supporting the lancet body 310 in the lancet holder 340 is mounted in the lancet holder 340.

A spiral guide protrusion 460 is formed around the inner side of the front case 130 inserted in the lancet holder housing 398 and a spiral guide groove 450 corresponding to the spiral guide protrusion 460 is formed around the outer side of the lancet holder housing 398.

Accordingly, when a user turns the front case 130 forward or backward, the front case 130 and the cap 140 move forward or backward, such that the protrusion length of the lancet 320 is adjusted.

Referring to FIG. 3, the front end of the stem 370 is connected with the lancet holder 340 by the connection pin 392 and a return spring 380 is fitted on a portion of the stem 370.

The front end of the return spring 380 elastically supports the holder housing 398 and the rear end is elastically supported by a step on the stem 370, such that the return spring 380 keeps elastically pushing the stem 370 rearward with respect to the holder housing 398.

Therefore, a rearward return force keeps applied to the stem 370 and the lancet holder 340 by the return spring 380.

Since the present invention relates to structures for operating and releasing of the rotary housing 360 and the stem 370, the other configurations are not described in detail.

Figure 5:
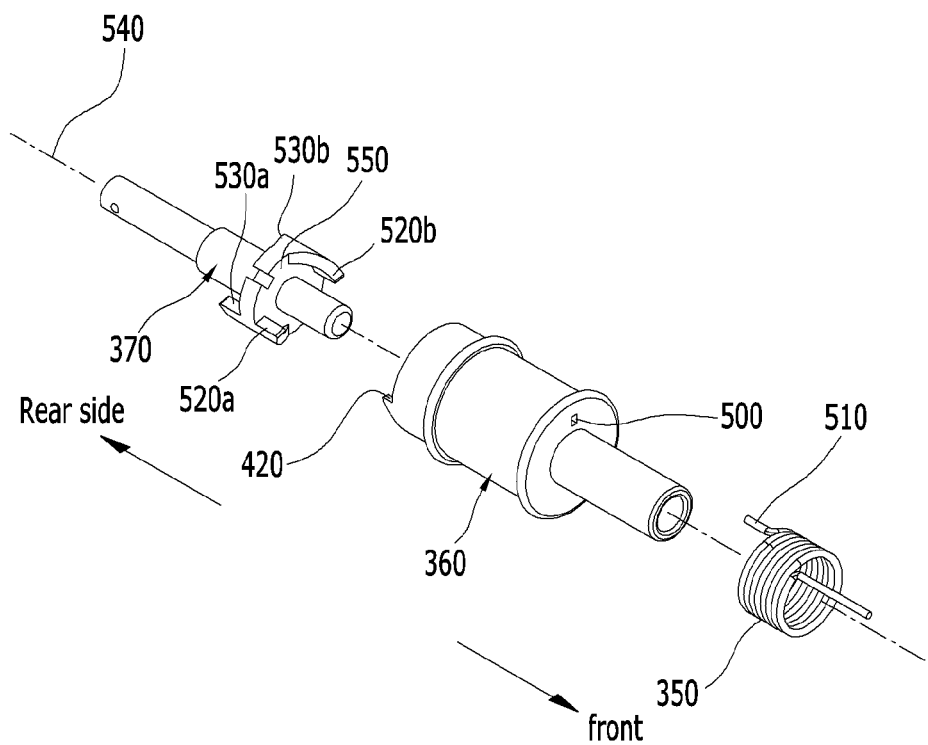
FIG. 5 is a partial exploded perspective view of a releasing mechanism of the lancing device according to an exemplary embodiment of the present invention.

FIG. 5 is a partial exploded perspective view of a releasing mechanism of the lancing device according to an exemplary embodiment of the present invention.

Referring to FIG. 5, the stem 370, the rotary housing 360, and the torsion spring 350 are arranged on a virtual rotation center axis 540 that coincides with a virtual straight line along which the stem 370 and the lancet holder 340 moves forward/backward.

An insertion hole 500 in which an end of the torsion spring 350 is inserted is formed at the rear side of the rotary housing 360 and the end 510 turns the rotary housing 360 forward about the rotation center axis 540 by the torque stored in the torsion spring 350.

As described above, when the locking protrusions 420 are unlocked from the anti-releasing protrusions 430 on the locker 399, the rotary housing 360 turns 180 degrees forward.

The front end of the stem 370 is connected with the lancet holder 340 by the connection pin 392 and the rear portion is inserted in the rotary housing 360. A disc 550 is formed at the rear portion of the stem 370 which is inserted in the rotary housing 360.

The disc 550 is formed in a circular plate shape extending radially from the rotation center axis 530, on the outer side of the stem 370.

A first forward-inclining rib 520a and a second forward-inclining rib 520b protrude rearward along the edge of the rear side of the disc 550 and a first backward-inclining rib 530a and a second backward-inclining rib 530b protrude forward along the edge of the front side of the disc 550.

The first forward-inclining rib 520a and the second forward-inclining rib 520b are formed at an interval of 180 degrees in the turning direction of the rotary housing 360, around the rotation center axis, and the first backward-inclining rib 530a and the second backward-inclining rib 530b are formed t an interval of 180 degrees in the turning direction of the rotary housing 360, corresponding to the first forward-inclining rib 520a and the second forward-inclining rib 520b.

The first forward-inclining rib 520a, the second forward-inclining rib 520b, the first backward-inclining rib 530a, and the second backward-inclining rib 530b each have an inclined surface that inclines in the turning direction of the rotary housing 360 and the end of the inclined surface makes an angle of about 90 degrees with the rear side or the front side of the disc 550.

Figure 6:
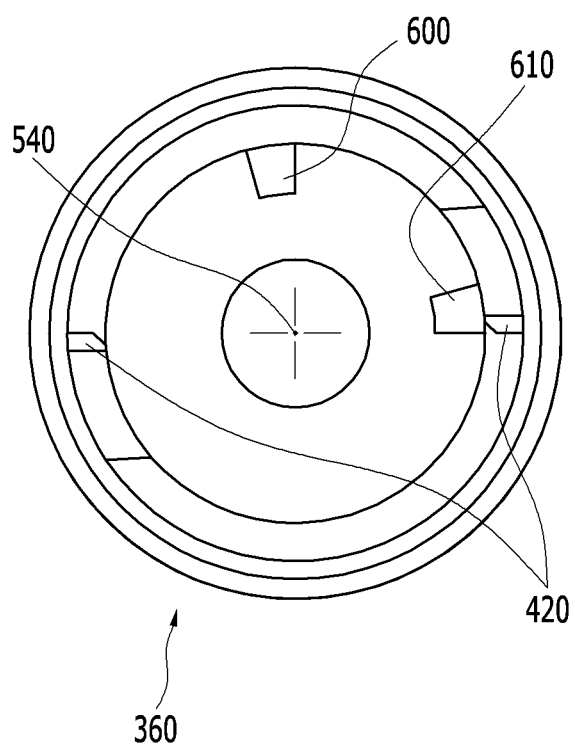
FIG. 6 is a side view of a rotary housing in the releasing mechanism of the lancing device according to an exemplary embodiment of the present invention.

FIG. 6 is a side view of the rotary housing in the releasing mechanism of the lancing device according to an exemplary embodiment of the present invention.

Referring to FIGS. 5 and 6, the rotary housing 360 has a cylindrical structure, in which a space with a circular inner side where the stem 370 is inserted is defined.

A forward rib 600 and a backward rib 610 are formed at an interval of 90 degrees around the rotation center axis 540, around the inner side of the rotary housing 360.

The forward rib 600 pushes the stem 370 forward using the inclined surface of the first forward rib 600 or the second forward rib 600 while turning at 180 degrees together with the rotary housing 360.

Further, the backward rib 610 pushes the stem 370 backward using the inclined surface of the first backward rib 610 or the second backward rib 610 while turning at 180 degrees together with the rotary housing 360.

Figure 7:
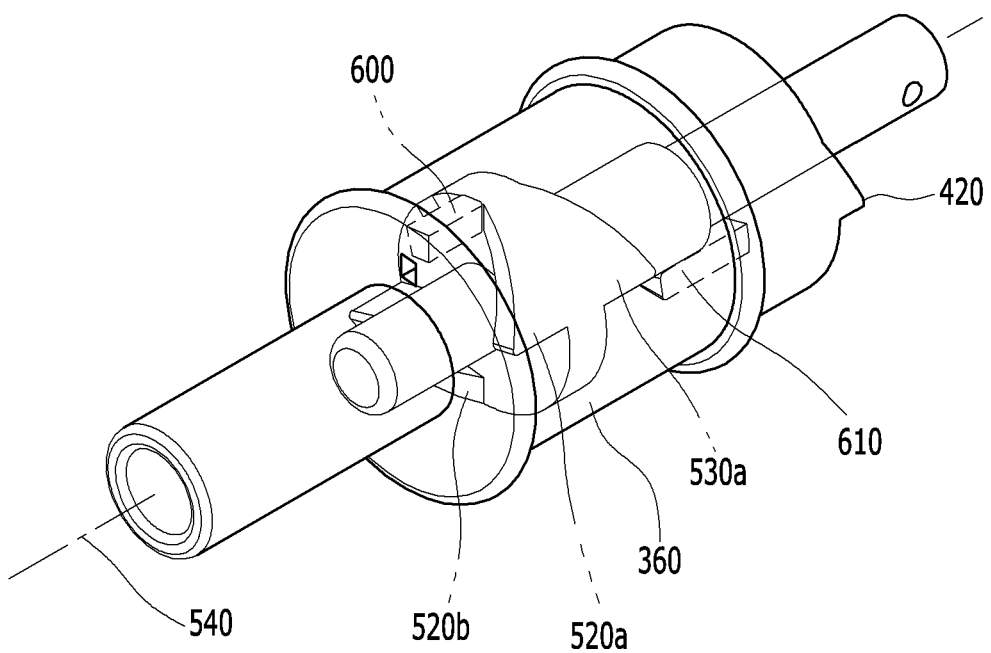
FIG. 7 is a partial perspective view before a stem moves forward in the releasing mechanism of the lancing device according to an exemplary embodiment of the present invention.
Figure 8:
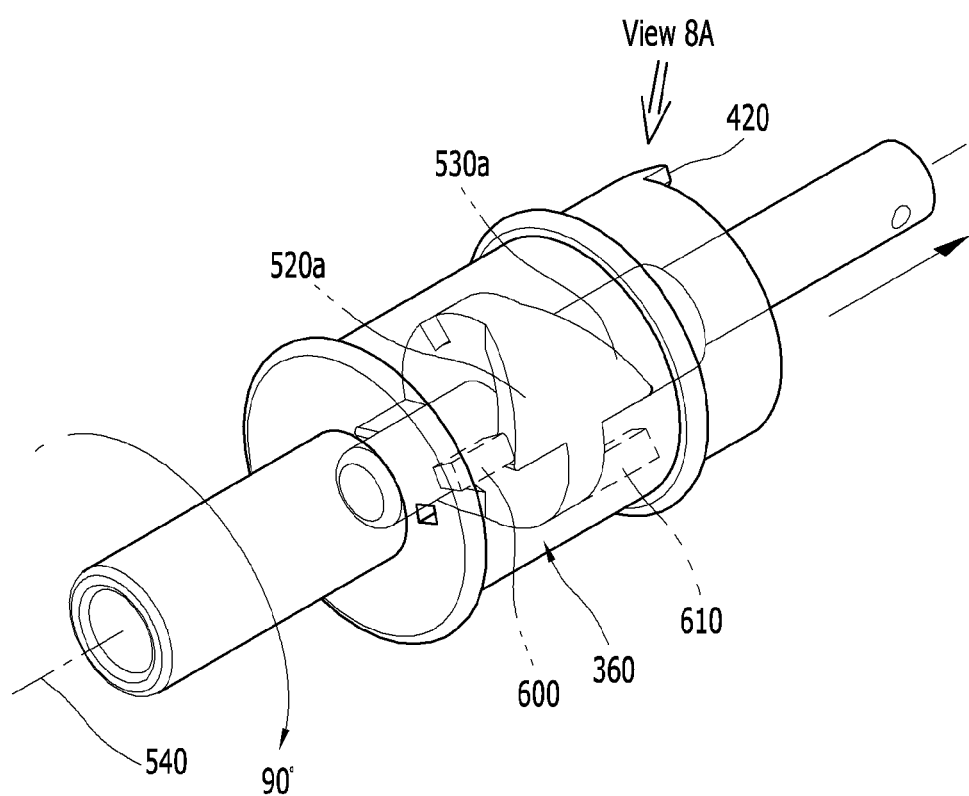
FIG. 8 is a perspective view when the stem moved forward in the releasing mechanism of the lancing device according to an exemplary embodiment of the present invention.

FIG. 7 is a partial perspective view before the stem moves forward in the releasing mechanism of the lancing device according to an exemplary embodiment of the present invention and FIG. 8 is a perspective view when the stem moved forward in the releasing mechanism of the lancing device according to an exemplary embodiment of the present invention.

Referring to FIG. 7, the forward rib 600 and the backward rib 610 are formed with a gap set in the longitudinal direction of the stem 370 and the forward rib 600 is in contact with the rear side of the disc 500, right before moving over the first forward-inclined surface 520a.

When the rotary housing 360 turns 90 degrees forward about the rotation center axis 540 in the position shown in FIG. 7, the operation status shown in FIG. 8 is achieved.

Referring to FIG. 8, as the rotary housing 360 turns 90 degrees, one side of the forward rib 600 moves the stem 370 forward while moving along the inclined surfaces of the forward-inclined ribs 520a and 520b.

Figure 9:
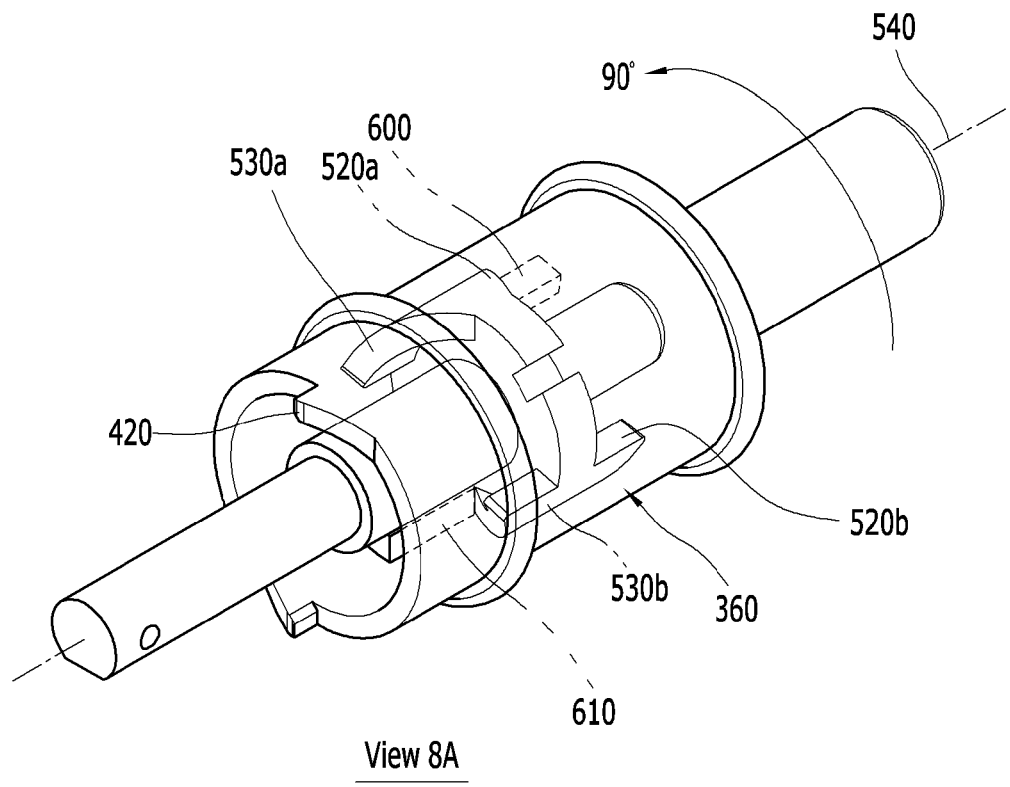
FIG. 9 is a perspective view seen from the view 8a in FIG. 8.

FIG. 9 is a perspective view seen from the view 8a in FIG. 8.

Referring to FIG. 9, the backward rib 610 is adjacent to the front side of the disc 550, right before moving over the inclined surface of the second backward-inclined surface 530b.

Figure 10:
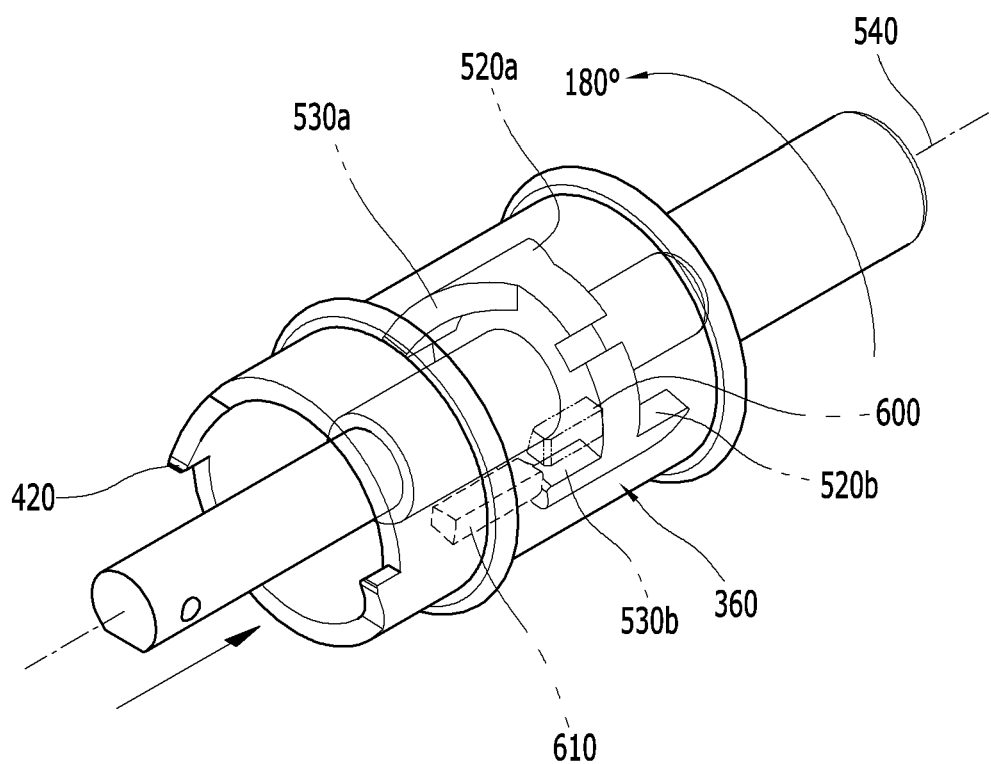
FIG. 10 is a perspective view when the stem moved back in the releasing mechanism of the lancing device according to an exemplary embodiment of the present invention.

When the rotary housing 360 further turns 90 degrees forward about the rotation center axis 540 in the position shown in FIG. 9, the operation status shown in FIG. 10 is achieved.

FIG. 10 is a perspective view when the stem moved back in the releasing mechanism of the lancing device according to an exemplary embodiment of the present invention.

Referring to FIG. 10, as the rotary housing 360 further turns 90 degrees, one side of the backward rib 610 forces the stem 370 to move backward while moving along the inclined surfaces of the backward-inclined ribs 530a and 530b.

Figure 11:
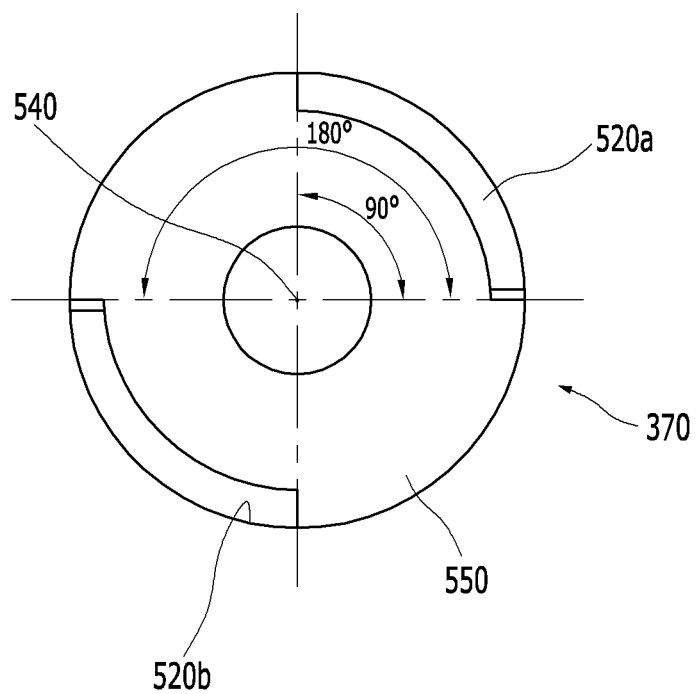
FIG. 11 is a side view of the stem in the releasing mechanism of the lancing device according to an exemplary embodiment of the present invention.

FIG. 11 is a side view of the stem in the releasing mechanism of the lancing device according to an exemplary embodiment of the present invention.

Referring to FIG. 11, the first forward-inclined rib 520a and the second forward-inclined surface 520b are formed with a rotational gap of 90 degrees on the rear side of the disc 550 on the stem 370.

The inclined surface of the first forward-inclined rib 520a is formed in the rotational range of 90 degrees and the inclined surface of the second forward-inclined rib 520b is also formed in the rotational range of 110 degrees. The portion without an inclined surface between the first forward-inclined rib 520a and the second forward-inclined rib 520b has a rotational range of about 90 degrees.

As described above, a sure structure for moving the lancet holder 340 and the lancet 320 together and preventing the lancet 320 from being stuck in the skin of a user (patient) is provided in an exemplary embodiment of the present invention.

Further, in an exemplary embodiment of the present invention, torque is stored in the torsion spring 350 by turning the loading handle 110 180 degrees forward and the rotary housing 360 is turned 180 degrees by the releasing switch 394, and in this structure, the first forward-inclined rib 520a and the second forward-inclined rib 520b are arranged with a gap of 180 degrees and the first backward-inclined rib 530a and the second backward-inclined rib 530b are arranged with a gap of 180 degrees.

However, in another exemplary embodiment of the present invention, it may be possible to store torque in the torsion spring 350 by turning the loading handle 110 360 degrees forward and to turn the rotary housing 360 360 degrees, using the releasing switch 394, and in this structure, only the first forward-inclined rib 520a may be disposed without the second forward-inclined rib 520b and only the first backward-inclined rib 530a without the second backward-inclined rib 530b.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A releasing structure for a lancing device, comprising:
   a lancet body with a lancet at a front of a lancing device;
   a lancet holder mounted with the lancet body with the lancet at the front of the lancing device;
   a stem disposed behind the lancet holder, the stem configured to move the lancet holder forward or backward;
   a rotary housing operably coupled to the stem, the rotary housing configured to push or pull the stem while turning forward at a predetermined angle about a rotational axis defined in a movement direction of the lancet, wherein a first end of the stem is connected to the lancet holder by a connection pin and a second end of the stem is inserted in the rotary housing;
   a torsion spring operably coupled to the rotary housing, the torsion spring configured to store torque for turning the rotary housing forward at a predetermined angle;
   a loading handle operably coupled to the torsion spring, the loading handle configured to transmit torque to the torsion spring while turning forward at a predetermined angle;
   a disc formed radially from a rotation center axis of the stem in the rotary housing, the disc being formed on a portion of the stem which is inserted in the rotary housing;
   a forward-inclined rib formed on a rear side of the disc, the forward-inclined rib being inclined within a predetermined range of angles in the movement direction;
   a backward-inclined rib formed on a front side of the disc, the backward-inclined rib corresponding to the forward-inclined rib;
   a forward rib protruding at a first side on an inner side of the rotary housing with the stem inserted, the forward rib corresponding to the forward-inclined rib, the forward rib configured to push the stem forward by moving along an inclined surface of the forward-inclined rib while turning with the rotary housing; and
   a backward rib protruding at a second side on the inner side of the rotary housing, the backward rib corresponding to the backward-inclined rib, the backward rib configured to push the stem backward by moving along an inclined surface of the backward-inclined rib while turning with the rotary housing.

2. The structure of claim 1, wherein the lancet body, the lancet holder, the stem, the rotary housing, the torsion spring, and the loading handle are sequentially arranged on a rotation center axis defined in the movement direction of the lancet.

3. The structure of claim 1, further comprising
   a case in which at least a portion of the lancet body, the lancet holder, the stem, the rotary housing, the torsion spring, or the loading handle is inserted,
   wherein an anti-reverse protrusion that prevents the loading handle from reversing is formed on an outer side of the loading handle and a locking protrusion corresponding to the anti-reverse protrusion is formed on an inner side of the case, and
   the anti-reverse protrusion is locked to the locking protrusion, after the loading handle transmits torque to the torsion spring by turning at a predetermined angle, such that the loading handle is prevented from reversing.

4. The structure of claim 3, wherein a locking protrusion is formed on the outer side of the rotary housing, at a predetermined distance from the rotation center axis, and the structure includes:
   a locker mounted on a side of the case and having an anti-releasing protrusion for preventing turning of the rotary housing by engaging with the locking protrusion;
   a releasing spring elastically supporting the locker to keep the anti-releasing protrusion engaging with the locking protrusion; and
   a releasing switch mounted on the case and pushing the locker against an elastic force of the releasing spring so that the anti-releasing protrusion is unlocked from the locking protrusion and the rotary housing is turned by the torque stored in the torsion spring.

5. The structure of claim 3, wherein an indication hole is formed at the case and a turning position of the loading handle or the rotary housing is sensed through the indication hole.

6. The structure of claim 1, wherein two forward-inclined ribs are formed with a gap of 180 degrees in a rotation direction on the rear side of the disc, and
two backward-inclined ribs are formed with a gap of 180 degrees in the rotation direction on the front side of the disc, corresponding to the forward-inclined ribs.

7. The structure of claim 1, wherein the forward rib comes in close contact with the inclined surface of the forward-inclined rib while turning with the rotary housing so that the stem moves forward,
the backward rib comes in close contact with the inclined surface of the backward-inclined rib while turning with the rotary housing so that the stem moves backward, and
the forward-inclined rib and the backward-inclined rib has a rotational difference of 90 degrees in a turning direction of the rotary housing.

8. The structure of claim 1, wherein the forward rib is in contact with the rear side of the disc, with the rotary housing turned 0 degrees, before releasing,
as the rotary housing turns 90 degrees, the forward rib pushes the stem forward by moving along the inclined surface of the forward-inclined rib and the backward rib is adjacent to the front side of the disc, and
as the rotary housing turns 180 degrees, the backward rib moves the stem backward by moving along the inclined surface of the backward-inclined rib.

9. The structure of claim 1, wherein the inclined surface of at least one of the forward-inclined ribs is formed within a range of 90 degrees in a turning direction of the rotary housing.

* * * * *